United States Patent
Ikeyama et al.

(10) Patent No.: US 9,512,100 B2
(45) Date of Patent: Dec. 6, 2016

(54) METHOD FOR PRODUCING GLYCOLIDE

(71) Applicant: Kureha Corporation, Tokyo (JP)

(72) Inventors: Yoshiko Ikeyama, Tokyo (JP); Nanako Saigusa, Tokyo (JP); Kensuke Suzuki, Tokyo (JP)

(73) Assignee: KUREHA CORPORATION, Tokyo (JP)

( * ) Notice: Subject to any disclaimer, the term of this patent is extended or adjusted under 35 U.S.C. 154(b) by 0 days.

(21) Appl. No.: 14/766,829

(22) PCT Filed: Mar. 25, 2014

(86) PCT No.: PCT/JP2014/058187
§ 371 (c)(1),
(2) Date: Aug. 10, 2015

(87) PCT Pub. No.: WO2014/157140
PCT Pub. Date: Oct. 2, 2014

(65) Prior Publication Data
US 2016/0002196 A1 Jan. 7, 2016

(30) Foreign Application Priority Data
Mar. 26, 2013 (JP) .................... 2013-063841

(51) Int. Cl.
C07D 319/12 (2006.01)
C08G 63/06 (2006.01)

(52) U.S. Cl.
CPC ............ *C07D 319/12* (2013.01); *C08G 63/06* (2013.01)

(58) Field of Classification Search
CPC .................................. C07D 319/12
USPC ....................................... 549/274
See application file for complete search history.

(56) References Cited

U.S. PATENT DOCUMENTS

| 5,618,911 A | 4/1997 | Kimura et al. |
| 5,714,618 A | 2/1998 | Kimura et al. |
| 5,830,991 A | 11/1998 | Shiiki et al. |
| 2003/0191326 A1 | 10/2003 | Yamane et al. |
| 2004/0116368 A1 | 6/2004 | Wen et al. |
| 2004/0122240 A1 | 6/2004 | Yamane et al. |
| 2011/0263875 A1 | 10/2011 | Suzuki et al. |

FOREIGN PATENT DOCUMENTS

| EP | 0 789 023 A2 | 8/1997 |
| JP | H05287056 A | 11/1993 |
| JP | H06287278 A | 10/1994 |
| JP | H07309862 A | 11/1995 |
| JP | H09328481 A | 12/1997 |
| JP | 3248597 B2 | 11/2001 |
| JP | 1446209 A | 10/2003 |
| JP | 2004523596 A | 8/2004 |
| KP | 2003-0040371 A | 5/2003 |
| WO | WO/02/14303 A1 | 2/2002 |
| WO | WO 02/083881 A1 | 10/2002 |
| WO | WO/2010/073512 A1 | 7/2010 |

OTHER PUBLICATIONS

International Search Report of PCT/JP2014/058187 dated Jun. 24, 2014.
Notification of the First Office Action issued Mar. 21, 2016, in Chinese Patent Application No. 201480004299.6, with English translation.
English translation of International Preliminary Report on Patentability and Written Opinion issued Oct. 8, 2015, in PCT International Application No. PCT/JP2014/058187.
Extended European Search Report issued Jul. 20, 2016, in European Patent Application No. 14775676.1.
Notification of Reason for Refusal issued Sep. 21, 2016, in Korean Patent Application No. 10-2015-7018421, with English translation.
Second Office Action issued Sep. 20, 2016, in Chinese Patent Application No. 201480004299.6, with English translation.

*Primary Examiner* — Taofiq A Solola
(74) *Attorney, Agent, or Firm* — Birch, Stewart, Kolasch & Birch, LLP

(57) ABSTRACT

A method for producing glycolide (GL) by heating a glycolic acid oligomer (GAO) to depolymerize the GAO. The method for producing GL comprises: a step 1 of heating a mixture containing a GAO having a terminal COOH concentration of 400 eq/t or less and a polar organic solvent to a GAO depolymerization temperature under ambient pressure or reduced pressure; a step 2 of continuing the heating at the temperature for depolymerizing of the GAO and then codistilling out the produced GL and the solvent from the depolymerization reaction system to the outside the reaction system; and a step 3 of obtaining GL from the codistillation product. In the method for producing GL, the GAO is preferably prepared by a GAO production method which comprises a step of condensing glycolic acid (GA) and a dehydration step of continuing the heating together with a polar organic solvent or a depolymerization reaction solution to allow the GA condensation reaction to continue.

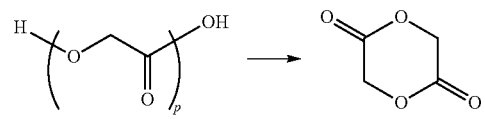

7 Claims, No Drawings

METHOD FOR PRODUCING GLYCOLIDE

TECHNICAL FIELD

The present invention relates to a method for producing highly pure glycolide efficiently and economically with long-term stability by means of the depolymerization of a glycolic acid oligomer.

Polyglycolic acid is a resin material having excellent biodegradability, hydrolyzability, gas barrier properties, strength, and the like. Polyglycolic acid is used, in a wide variety of technical fields, as polymer materials for medical purposes such as suture threads and artificial skins; packaging materials such as bottles and films; resin materials for various industrial products such as injection molded products, fibers, deposited films, and fishing lines; resin materials for well drilling and completion; and the like.

Polyglycolic acid is a polymer having a repeating unit of a structure formed by dehydrative polycondensation of glycolic acid. However, the method in which glycolic acid is subjected to dehydrative polycondensation as a starting raw material only provides polyglycolic acid having a low degree of polymerization. Polyglycolic acid having a low degree of polymerization exhibits insufficient strength, melt processability, gas barrier properties, and the like. Furthermore, polyglycolic acid having a low degree of polymerization cannot satisfy durability requirements when applied in various uses since the rate of degradation thereof in a natural condition or in vivo is too fast.

Furthermore, in the method in which glycolic acid is subjected to dehydrative polycondensation as a starting raw material, control of the degree of polymerization of the polyglycolic acid is difficult, and in particular, it is extremely difficult to synthesize polyglycolic acid having a high degree of polymerization with the existing state of the art. Furthermore, even when polycondensation by dealcoholization is performed using alkyl glycolate as a starting raw material, synthesis of polyglycolic acid having a high degree of polymerization is difficult.

According to a method in which glycolide, which is a cyclic dimer of glycolic acid, is used as a starting raw material and is subjected to ring-opening polymerization, control of the degree of polymerization of the polyglycolic acid is easy, and polyglycolic acid having a high degree of polymerization can be synthesized. Glycolide is a cyclic ester compound having a cyclic dimer structure where two molecules of water are eliminated from two molecules of glycolic acid. However, even when glycolic acids are subjected to dehydration reaction, it is not possible to synthesize glycolides and only glycolic acid oligomers having a low degree of polymerization are provided.

As a method for producing glycolide, a method of depolymerizing glycolic acid oligomers has been known. Specifically, a glycolic acid oligomer having a low degree of polymerization is synthesized by polycondensing glycolic acid in accordance with reaction formula 1 below:

[Formula 1]

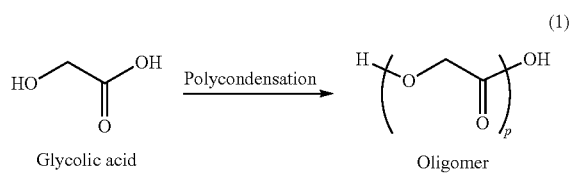

Thereafter, glycolide is synthesized by depolymerizing the glycolic acid oligomer in accordance with reaction formula 2 below:

[Formula 2]

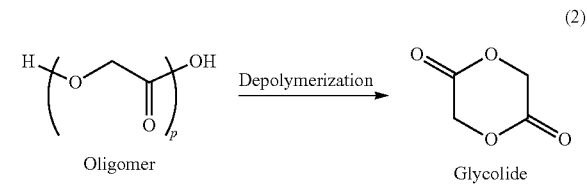

Polyglycolic acid can be produced by subjecting the glycolide to ring-opening polymerization in accordance with reaction formula 3 below:

[Formula 3]

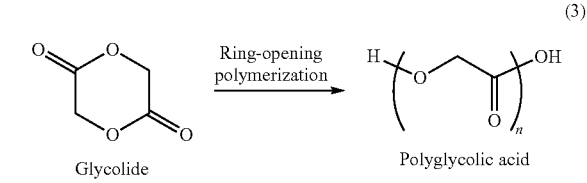

Various methods have been proposed as methods for synthesizing glycolide via depolymerization of glycolic acid oligomers. As a method suitable for mass production of glycolide, a solution phase depolymerization method has been proposed. The solution phase depolymerization method is a method of performing depolymerization by heating a mixture containing a glycolic acid oligomer and a polar organic solvent to form a solution phase of the glycolic acid oligomer, and continuing the heating in this condition. When the solubility toward the polar organic solvent of the glycolic acid oligomer needs to be increased, a solubilizing agent is contained in the mixture.

Patent Document 1 discloses a method for producing a dimeric cyclic ester, the method comprising the steps of: heating an -hydroxycarboxylic acid oligomer, such as a glycolic acid oligomer, in a high-boiling-point polar organic solvent; dissolving the oligomer; further continuing the heating in this condition to depolymerize the oligomer; distilling off the produced dimeric cyclic ester with the polar organic solvent; and recovering the dimeric cyclic ester, such as glycolide, from the distillate.

Patent Document 2 discloses a method for producing a cyclic ester, the method comprising the steps of: heating a mixture containing aliphatic polyester, such as low molecular weight polyglycolic acid, and a particular polyalkylene glycol ether to a temperature at which depolymerization of the aliphatic polyester takes place; forming a substantially homogeneous solution phase and depolymerizing the aliphatic polyester in the substantially homogeneous solution phase; distilling off the cyclic ester formed by the depolymerization together with the polyalkylene glycol ether; and recovering the cyclic ester, such as glycolide, from the distillate.

Patent Document 3 discloses a method for producing glycolide, the method comprising continuously performing depolymerization reaction by charging a glycolic acid oligomer or a mixture of a glycolic acid oligomer and a polar organic solvent continuously or intermittently into a depolymerization reaction system containing the glycolic acid oligomer and the polar organic solvent, and controlling the amount of a compound having an alcoholic hydroxyl group.

The methods disclosed in Patent Documents 1 to 3 enable stable depolymerization reaction as well as mass production of glycolide. In particular, according to the method disclosed in Patent Document 3, production of heavy materials and decrease in rate of production of glycolide due to impurities accumulated in the depolymerization reaction system can be suppressed even when the depolymerization reaction is continuously or repeatedly performed in the same reaction vessel.

By using the solution phase depolymerization methods disclosed in Patent Documents 1 to 3, it is possible to perform continuous operation for a relatively long period of time when the depolymerization reaction is continuously performed in the same equipment while a glycolic acid oligomer is charged continuously or intermittently into the depolymerization reaction system containing the glycolic acid oligomer and a polar organic solvent. However, when this continuous operation is performed for a long period of time, e.g. several months or longer, by this method, it was found that lines including pipes, heat exchangers, and the like are plugged.

In the depolymerization reaction, depolymerization is performed by heating a mixture containing a glycolic acid oligomer and a polar organic solvent in a reaction vessel, and the produced glycolide is codistilled with the polar organic solvent. The codistillation product is directed to the outside of the depolymerization reaction system through a line such as a pipe and/or heat exchanger. The depolymerization reaction is typically performed under reduced pressure. The codistillation product is liquefied by cooling via a heat exchanger. Glycolide is recovered from the liquid codistillation product. The polar organic solvent contained in the codistillation product is refluxed to the depolymerization reaction system. Additional glycolic acid oligomer is supplied to the depolymerization reaction system to replenish the glycolic acid oligomer consumed by the depolymerization.

Although it is possible to perform continuous operation for a relatively long period of time according to this method, when the operation period of the continuous operation is extended, it was found that impurities contained in the depolymerization reaction system act as a polymerization initiator and plug the line by oligomerizing a part of the formed glycolide. When the line is plugged, the predetermined degree of pressure reduction cannot be maintained, thereby making it impossible to continue the operation. Therefore, the entire equipment including the line, such as pipes and heat exchangers, needs to be cleaned by stopping the operation after a fixed time period has passed. The cleaning takes approximately two to three weeks depending on the scale and structure of the equipment. Frequent stop of operation and cleaning treatment directly leads to high production costs of glycolide.

Conventional glycolide obtained by depolymerization of glycolic acid oligomer has insufficient purity, and thus is called crude glycolide. Glycolide used as a monomer for ring-opening polymerization is required to have a high purity of 99.9% or higher. Therefore, the crude glycolide obtained by depolymerization is purified by a purification treatment such as recrystallization or washing. If the purity of the crude glycolide is low, purification costs cannot be lowered and also plugging of the line during the purification step may be caused.

A major cause for the line plugging during the depolymerization reaction is considered to be oligomers attached to the surface of each part of the equipment, the oligomers being formed in the middle of the line by oligomerization of glycolide, formed and distilled by the depolymerization, due to impurities, contained in the fraction that is distilled from the depolymerization reaction system, acting as a polymerization initiator. In fact, the crude glycolide obtained by the depolymerization contains various impurities.

These impurities are considered to not only increase the amount of impurities by reacting with produced glycolide in the depolymerization reaction system containing a glycolic acid oligomer and a polar organic solvent, but also cause ring-opening polymerization of the glycolide in the middle of the line and become a cause of the line plugging in the continuous operation for a long period of time. As a method of reducing impurities, a method of highly purifying the raw material glycolic acid, a method of purifying the glycolic acid oligomer, and a method combining these could be employed; however, costs of these methods are high.

Patent Document 4 discloses a method of obtaining highly pure glycolide by employing a method of performing depolymerization of a glycolic acid oligomer after a mixture containing the glycolic acid oligomer and a high-boiling-point polar organic solvent is subjected to a total reflux treatment. That is, by the method for producing glycolide comprising a step of performing a total reflux treatment under conditions where a mixture containing a glycolic acid oligomer and a high-boiling-point polar organic solvent having a boiling point within a range of 230 to 450° C. is heated under ambient pressure or reduced pressure to reflux and, at this time, substantially all the amount of the distillate that is distilled from the reflux system containing the mixture is refluxed to the reflux system for a reflux time within a range of 0.1 to 20 hours, it is possible to reduce the amount of impurities in the distillate that is distilled from the depolymerization reaction system, and suppress the plugging of the line due to oligomerization of glycolide caused by the impurities, thereby making it possible to obtain highly pure glycolide via the depolymerization.

"Total reflux treatment" refers to a treatment in which all the fractions distilled in the reflux treatment are cooled and then substantially all the amount of the distillate is returned to the reflux system composed of the original mixture. Therefore, the distillate, such as the polar organic solvent, is not discharged from the reflux system during the total reflux treatment.

Since the total reflux treatment continues the operation in which the mixture containing the glycolic acid oligomer and the polar organic solvent is heated to distill, then the distilled total fraction is cooled, and substantially all the amount of the distillate is returned to the reflux system composed of the original mixture, there are concerns for newly adding thermal history to the glycolic acid oligomer and the polar organic solvent, and a problem in that the amount of consumption of thermal energy for the distillation is increased.

Therefore, a method for producing glycolide that provides highly pure glycolide via depolymerization, the method involving no new thermal history unlike the total reflux treatment, contributing to energy conservation, lowering the amount of impurities in the distillate that is distilled from the depolymerization reaction system, and suppressing the plugging of the line due to oligomerization of glycolide caused by impurities, has been desired.

Note that Patent Document 5 discloses a method for producing aliphatic polyester, the method comprising: producing a precursor polymer of poly(-hydroxy acid) having a reduced viscosity of 0.1 dL/g or greater and a carboxyl group concentration of 200 eq/$10^6$ g or less (which is the same as "200 eq/t or less"), and then subjecting a cyclic dimer (lactides), obtained by heat-depolymerizing the precursor polymer, to ring-opening polymerization; however, the method was not practical as a method of depolymerization to obtain lactide or glycolide, which is a cyclic dimer, from the precursor polymer of the poly(-hydroxy acid) because the method requires high vacuum conditions that are a temperature of 210° C. or 230° C. and a pressure of 0.05 mmHg (equivalent to 0.0067 kPa).

CITATION LIST

Patent Literature

[Patent Document 1] Japanese Unexamined Patent Application Publication No. H09-328481A (corresponding to U.S. Pat. No. 5,830,991)
[Patent Document 2] WO/2002/014303 (corresponding to US Patent Application No. 2003/0191326)
[Patent Document 3] Japanese Unexamined Patent Application Publication (Translation of PCT Application) No. 2004-523596A (corresponding to US Patent Application No. 2004/0122240)
[Patent Document 4] WO/2010/073512 (corresponding to US Patent Application No. 2011/0263875)
[Patent Document 5] Japanese Unexamined Patent Application Publication No. H05-287056A

SUMMARY OF INVENTION

Technical Problem

An object of the present invention is to provide a method for producing glycolide that provides highly pure glycolide via depolymerization, the method involving no new thermal history unlike total reflux treatment, contributing to energy conservation, lowering the amount of impurities in the distillate that is distilled from the depolymerization reaction system, and suppressing the plugging of the line due to oligomerization of glycolide caused by impurities.

Solution to Problem

Through the research to solve the object described above, the present inventors have found that, in the method for producing glycolide by depolymerizing a glycolic acid oligomer, highly pure glycolide can be continuously obtained by lowering the terminal carboxyl group concentration of a resulting glycolic acid oligomer when the glycolic acid oligomer, which is a raw material of depolymerization, is produced, and thus completed the present invention.

That is, the present invention provides a method for producing glycolide by heating a glycolic acid oligomer to depolymerize, the method comprising the steps below:
I. a step 1 of heating a mixture containing a glycolic acid oligomer having a terminal carboxyl group concentration of 400 eq/t or less and a polar organic solvent to a temperature for depolymerizing the glycolic acid oligomer under ambient pressure or reduced pressure;
II. a step 2 of continuing the heating at the temperature for depolymerizing the glycolic acid oligomer and then codistilling out, together with the polar organic solvent, glycolide produced by the depolymerization from the depolymerization reaction system containing the mixture; and
III. a step 3 of obtaining glycolide from the codistillation product.

The present invention also provides the following methods (1) to (8) for producing glycolide as embodiments.
(1) The method for producing glycolide described above, wherein the glycolic acid oligomer is a glycolic acid oligomer having a terminal carboxyl group concentration of 250 eq/t or less.
(2) The method for producing glycolide described above, wherein the glycolic acid oligomer having the terminal carboxyl group concentration of 400 eq/t or less is prepared by a method for producing a glycolic acid oligomer comprising a condensing step of subjecting glycolic acid to condensation reaction by heating the glycolic acid under ambient pressure or reduced pressure, and a dehydration step of continuing the condensation reaction of the glycolic acid by continuing the heating together with a polar organic solvent under ambient pressure or reduced pressure.
(3) The method for producing glycolide described above, wherein the glycolic acid oligomer having the terminal carboxyl group concentration of 400 eq/t or less is prepared by a method for producing a glycolic acid oligomer comprising a condensing step of subjecting glycolic acid to condensation reaction by heating the glycolic acid under ambient pressure or reduced pressure, and a dehydration step of continuing the condensation reaction of the glycolic acid by continuing the heating together with a depolymerization reaction solution obtained from a depolymerization reaction system and, if necessary, the polar organic solvent under ambient pressure or reduced pressure.
(4) The method for producing glycolide described above, wherein the dehydration step is performed in the presence of a solubilizing agent.
(5) The method for producing glycolide described above, wherein the mixture in the step 1 contains a solubilizing agent.
(6) The method for producing glycolide described above, wherein the dehydration step is performed in the presence of a catalyst.
(7) The method for producing glycolide described above, wherein the polar organic solvent is polyalkylene glycol diether having a molecular weight of 150 to 450.
(8) The method for producing glycolide described above, wherein the solubilizing agent is polyalkylene glycol monoether having a boiling point of 180° C. or higher.

Advantageous Effects of Invention

Since the present invention is a method for producing glycolide by heating a glycolic acid oligomer to depolymerize, the method comprising the steps below:
I. a step 1 of heating a mixture containing a glycolic acid oligomer having a terminal carboxyl group concentration of 400 eq/t or less and a polar organic solvent to a temperature for depolymerizing the glycolic acid oligomer under ambient pressure or reduced pressure;
II. a step 2 of continuing the heating at the temperature for depolymerizing the glycolic acid oligomer and then codistilling out, together with the polar organic solvent, glycolide produced by the depolymerization from the depolymerization reaction system containing the mixture; and
III. a step 3 of obtaining glycolide from the codistillation product;
the present invention can provide a method for producing glycolide that provides highly pure glycolide via depolymerization, the method involving no new thermal history due to total reflux treatment, contributing to energy conservation, lowering the amount of impurities in the distillate that is distilled from the depolymerization reaction system, and suppressing the plugging of the line due to oligomerization of glycolide caused by impurities.

DESCRIPTION OF EMBODIMENTS

1. Glycolic Acid Oligomer Having Terminal Carboxyl Group Concentration of 400 eq/t or Less The method for producing glycolide of the present invention is a method for producing glycolide by heating a glycolic acid oligomer to depolymerize, and the glycolic acid oligomer is a glycolic acid oligomer having a terminal carboxyl group concentration of 400 eq/t or less.

The glycolic acid oligomer (hereinafter, also referred to as "GAO"), which is the starting raw material of the method for producing glycolide of the present invention, is a (co)polymer of glycolic acid having a weight average molecular weight of 3000 or greater, preferably 5000 or greater, and more preferably 7000 or greater. The upper limit of the weight average molecular weight of the GAO is ordinarily approximately 20,000 and in many cases approximately 15,000. The weight average molecular weight is a value measured using gel permeation chromatography (GPC). The GAO can be obtained by subjecting glycolic acid (this glycolic acid may be an ester or salt of glycolic acid) to condensation reaction. After the completion of the condensation reaction, the produced GAO may be used as is as a raw material for producing glycolide, or the produced GAO may be used after removing unreacted substances, low polymers, catalysts, or the like by washing with a non-solvent for GAO such as benzene or toluene. The melting point (Tm) of the GAO is typically 140° C. or higher, preferably 160° C. or higher, and more preferably 180° C. or higher, from the perspective of the yield of glycolide at the time of depolymerization reaction. The melting point is a temperature detected using a differential scanning calorimeter (DSC). The upper limit of the melting point of the GAO is approximately 220° C.

Terminal Carboxyl Group Concentration

The GAO used in the present invention is a GAO having a terminal carboxyl group concentration of 400 eq/t or less. The terminal carboxyl group concentration of the GAO is measured by the following method. That is, 0.1 g of GAO is completely dissolved in 10 mL of special grade dimethylsulfoxide in an oil bath at a temperature of 150° C. for approximately 3 minutes. After adding two drops of an indicator (0.1% by mass of bromothymol blue/alcohol solution) to this solution, 0.05 N of diazabicycloundecene/dimethylsulfoxide solution is added until an end point, where color of the solution has changed from yellow to blue when observed visually, is reached. From the dropped amount of the indicator at the point, the terminal carboxyl group concentration of the GAO is calculated as the equivalent amount (eq) per 1 ton (t) of the GAO. Furthermore, the terminal carboxyl group concentration of GAO contained in the mixture containing the GAO and the polar organic solvent is measured by the following method. That is, 0.1 g of the mixture is completely dissolved in 10 mL of special grade dimethylsulfoxide in an oil bath at a temperature of 150° C. for approximately 3 minutes. After adding two drops of the indicator described above to this solution, 0.009 N of diazabicycloundecene/dimethylsulfoxide solution is added until an end point, where color of the solution has changed from yellow to blue when observed visually, is reached. From the dropped amount of the indicator at the point, the terminal carboxyl group concentration of the GAO is calculated as the equivalent amount (eq) per 1 ton (t) of the mixture, and then, by dividing the calculated equivalent amount by the mass proportion of the GAO in the mixture, the terminal carboxyl group concentration of the GAO is calculated as the equivalent amount (eq) per 1 ton (t) of the GAO. The terminal carboxyl group concentration of the GAO is preferably 360 eq/t or less, more preferably 250 eq/t or less, and even more preferably 245 eq/t or less. As described below, when the dehydration step is performed in the presence of a catalyst, the terminal carboxyl group concentration of the GAO can be set to 160 eq/t or less, furthermore, 150 eq/t or less, or as desired, 140 eq/t or less. The lower limit of the terminal carboxyl group concentration of the GAO is not particularly limited; however, the lower limit is typically approximately 50 eq/t, and in many cases approximately 70 eq/t. When the terminal carboxyl group concentration of the GAO is too high, in the method for producing glycolide by heating the GAO to depolymerize, highly pure glycolide cannot be obtained, and continuous operation for a long period of time may be made difficult due to plugging of the production line of the glycolide.

Preparation of Glycolic Acid Oligomer Having a Terminal Carboxyl Group Concentration of 400 eq/t or Less The GAO having the terminal carboxyl group concentration of 400 eq/t or less can be prepared by a method for producing a glycolic acid oligomer comprising a condensing step of subjecting glycolic acid to condensation reaction by heating the glycolic acid under ambient pressure or reduced pressure, and a dehydration step of continuing the condensation reaction of the glycolic acid by continuing the heating together with a polar organic solvent under ambient pressure or reduced pressure.

Specifically, a condensing step is first performed by heating glycolic acid (this glycolic acid may be an ester or salt of glycolic acid) as an aqueous solution (70% aqueous solution can be acquired as a commercially available product) at a temperature of typically from 100 to 250° C., and preferably from 140 to 230° C., for 30 minutes to 15 hours, preferably 1 to 10 hours, while being stirred under ambient pressure or reduced pressure to perform condensation reaction while water or the like is distilled. The condensing step does not require use of a condensation catalyst or a transesterification catalyst; however, the condensation reaction may be performed in the presence of a catalyst such as a tin compound or antimony compound. The condensing step may be performed under ambient pressure or reduced pressure, and specifically may be performed under reduced pressure of 0.1 to 90 kPa, and preferably 1 to 60 kPa; however, the condensing step is preferably performed under ambient pressure.

The GAO having a terminal carboxyl group concentration of 400 eq/t or less can be prepared by performing a dehydration step of continuing the condensation reaction of the glycolic acid by continuing the heating together with a polar organic solvent under ambient pressure or reduced pressure, following the condensing step.

Polar Organic Solvent

As the polar organic solvent used in the dehydration step, a polar organic solvent that is used as a solvent for depolymerization reaction of GAOs can be used. Specifically, a polar organic solvent having a boiling point under ambient pressure of 230 to 450° C., preferably 255 to 430° C., and more preferably 280 to 420° C., can be used. Furthermore, the molecular weight of the polar organic solvent is preferably in a range of 150 to 450, more preferably 180 to 420, and even more preferably 200 to 400. The used amount of the polar organic solvent in the dehydration step is typically from 10 to 100 parts by mass, preferably from 15 to 80 parts by mass, and more preferably from 18 to 60 parts by mass, per 100 parts by mass of glycolic acid. By performing the dehydration step in the presence of the polar organic solvent, the condensation reaction and/or dehydration reaction of glycolic acid proceeds efficiently.

Examples of the polar organic solvent include aromatic dicarboxylic acid diesters, aromatic carboxylic acid esters, aliphatic dicarboxylic acid diesters, polyalkylene glycol diethers, aromatic dicarboxylic acid dialkoxy alkyl esters, aliphatic dicarboxylic acid dialkoxy alkyl esters, polyalkylene glycol diesters, aromatic phosphates, and the like.

Among these polar organic solvents, aromatic dicarboxylic acid diesters, aromatic carboxylic acid esters, aliphatic dicarboxylic acid diesters, and polyalkylene glycol diethers are preferable. From the perspective of causing less thermal degradation, polyalkylene glycol diethers are more preferable, and polyalkylene glycol diethers having a molecular weight of 150 to 450 are particularly preferable.

Examples of the aromatic dicarboxylic acid diester include phthalic acid esters such as dibutyl phthalate, dioctyl phthalate, dibenzyl phthalate, and benzyl butyl phthalate. Examples of the aromatic carboxylic acid ester include benzoic acid esters such as benzyl benzoate. Examples of the aliphatic dicarboxylic acid diester include adipic acid esters, such as dioctyl adipate, and sebacic acid esters, such as dibutyl sebacate.

Examples of the polyalkylene glycol diether having a molecular weight of 150 to 450 that is particularly preferably used include polyethylene glycol dialkyl ethers, such as diethylene glycol dibutyl ether, diethylene glycol dihexyl ether, diethylene glycol dioctyl ether, diethylene glycol butyl 2-chlorophenyl ether, triethylene glycol diethyl ether, triethylene glycol dipropyl ether, triethylene glycol dibutyl ether, triethylene glycol dihexyl ether, triethylene glycol dioctyl ether, triethylene glycol butyloctyl ether, triethylene glycol butyldecyl ether, tetraethylene glycol diethyl ether, tetraethylene glycol dipropyl ether, tetraethylene glycol dibutyl ether, tetraethylene glycol dihexyl ether, tetraethylene glycol dioctyl ether, diethylene glycol butylhexyl ether, diethylene glycol butyloctyl ether, diethylene glycol hexyloctyl ether, triethylene glycol butylhexyl ether, triethylene glycol hexyloctyl ether, tetraethylene glycol butylhexyl ether, tetraethylene glycol butyloctyl ether, and tetraethylene glycol hexyloctyl ether; polyalkylene glycol dialkyl ethers, such as polypropylene glycol dialkyl ether or polybutylene glycol dialkyl ether, having a propyleneoxy group or butyleneoxy group instead of the ethyleneoxy group in the polyethylene glycol dialkyl ether; diethylene glycol butylphenyl ether, diethylene glycol hexylphenyl ether, diethylene glycol octylphenyl ether, triethylene glycol butylphenyl ether, triethylene glycol hexylphenyl ether, triethylene glycol octylphenyl ether, tetraethylene glycol butylphenyl ether, tetraethylene glycol hexylphenyl ether, tetraethylene glycol octylphenyl ether, or polyethylene glycol alkyl aryl ether of these compounds in which hydrogen of the phenyl group is substituted with alkyl, alkoxy, halogen, or the like; polyalkylene glycol alkyl aryl ethers, such as polypropylene glycol alkyl aryl ether or polybutylene glycol alkyl aryl ether, having a propyleneoxy group or butyleneoxy group instead of the ethyleneoxy group in the polyethylene glycol alkyl aryl ether; polyethylene glycol diaryl ethers, such as diethylene glycol diphenyl ether, triethylene glycol diphenyl ether, tetraethylene glycol diphenyl ether, or a compound in which the phenyl group of these compounds is substituted with alkyl, alkoxy, halogen, or the like; polyalkylene glycol diaryl ethers, such as polypropylene glycol diaryl ether or polybutylene glycol diaryl ether, having a propyleneoxy group or butyleneoxy group instead of the ethyleneoxy group in the polyethylene glycol diaryl ether; and the like.

Solubilizing Agent

Although a polar organic solvent only can be used in the dehydration step, the dehydration step is preferably performed in the presence of a solubilizing agent from the perspective of further enhancing the purity of the glycolide obtained by the depolymerization. The solubilizing agent is preferably a compound which satisfies any one or more of the following requirements.

(1) The solubilizing agent is a non-basic compound. Basic compounds such as amine, pyridine, and quinoline are not preferable since the basic compounds may react with aliphatic polyester or produced cyclic ester.

(2) The solubilizing agent is a compound which is compatible with or soluble in a polar organic solvent such as polyalkylene glycol diether. The solubilizing agent may be a liquid or a solid at room temperature as long as it is a compound which is compatible with or soluble in the polar organic solvent.

(3) The solubilizing agent is a compound having a boiling point of at least 180° C., preferably at least 200° C., more preferably at least 230° C., and particularly preferably at least 250° C.

(4) The solubilizing agent is a compound having a functional group such as an OH group, a COOH group, a CONH group, or the like.

(5) The solubilizing agent has a higher affinity toward glycolic acid oligomers than that of the polar organic solvent.

As the solubilizing agent, monohydric alcohols and polyhydric alcohols are particularly effective. As the monohydric or polyhydric alcohol, a monohydric or polyhydric alcohol having a boiling point of 180° C. or higher, preferably 200° C. or higher, more preferably 230° C. or higher, and particularly preferably 250° C. or higher, can be used.

Examples of the monohydric or polyhydric alcohol include aliphatic alcohols such as decanol, tridecanol, decanediol, ethylene glycol, propylene glycol, and glycerin; aromatic alcohols such as cresol, chlorophenol, and naphthyl alcohol; polyalkylene glycols such as polyethylene glycol, propylene glycol, and polybutylene glycol; polyalkylene glycol monoethers; and the like. The polyalkylene glycol monoether having a boiling point of 180° C. or higher is particularly preferable.

Specific examples of the polyalkylene glycol monoether include polyethylene glycol monoethers such as polyethylene glycol monomethyl ether, polyethylene glycol monoethyl ether, polyethylene glycol monopropyl ether, polyethylene glycol monobutyl ether, polyethylene glycol monohexyl ether, polyethylene glycol monooctyl ether, polyethylene glycol monodecyl ether, and polyethylene glycol monolauryl ether; polyalkylene glycol monoethers, such as polypropylene glycol monoether or polybutylene glycol monoether, in which an ethyleneoxy group is substituted with a propyleneoxy group or butyleneoxy group in the polyethylene glycol monoether; and the like.

The polyalkylene glycol monoether is more preferably a polyalkylene glycol monoether having an alkyl group having from 1 to 18 carbons as its ether group, and even more preferably a polyalkylene glycol monoether having an alkyl group having from 6 to 18 carbons as its ether group. These may be respectively used alone or in combination of two or more types. Among the polyalkylene glycol monoethers, polyethylene glycol monoalkyl ether such as triethylene glycol monooctyl ether (octyl triethylene glycol) is preferable.

When the dehydration step is performed in the presence of the solubilizing agent, the used amount of the solubilizing agent is typically from 10 to 100 parts by mass, preferably from 15 to 80 parts by mass, and more preferably from 18 to 60 parts by mass, per 100 parts by mass of glycolic acid. Furthermore, the dehydration step does not require use of a condensation catalyst or a transesterification catalyst; however, the dehydration step may be performed in the presence of a catalyst such as a tin compound (e.g. tin chloride) or antimony compound. The used amount of the catalyst is typically from 10 to 100 mg, preferably from 15 to 80 mg, and more preferably from 18 to 60 mg, per 100 parts by mass of glycolic acid.

The dehydration step is performed by continuing the condensation reaction of the glycolic acid by continuing the heating of the mixture containing the glycolic acid, the polar organic solvent, and, if necessary, the solubilizing agent under ambient pressure or reduced pressure, preferably under a reduced pressure of 0.1 to 90 kPa, more preferably 1 to 60 kPa, even more preferably 1.5 to 40 kPa, and particularly preferably 2 to 30 kPa. The temperature at which the dehydration step is performed is a temperature that can continue the condensation reaction, which is typically from 100 to 250° C., preferably from 120 to 230° C., more preferably from 130 to 224° C., and even more preferably from 140 to 221° C., and that is lower than the boiling point of the polar organic solvent but that can boil or discharge low-boiling point components such as water and unreacted raw materials. The time period for performing the dehydration step is typically from 30 minutes to 12 hours, preferably from 1 to 10 hours, and more preferably from 2 to 9 hours, and it is sufficient if the dehydration step is continued until the terminal carboxyl group concentration of the obtained GAO becomes 400 eq/t or less, and preferably 250 eq/t or less.

Furthermore, the dehydration step can be also performed by using a depolymerization reaction solution that is described below in addition to the polar organic solvent described above or in place of the polar organic solvent. That is, the GAO having the terminal carboxyl group concentration of 400 eq/t or less can be prepared by a method for producing a GAO comprising a condensing step of subjecting glycolic acid to condensation reaction by heating the glycolic acid under ambient pressure or reduced pressure, and a dehydration step of continuing the condensation reaction of the glycolic acid by continuing the heating together with a depolymerization reaction solution obtained from a depolymerization reaction system and, if necessary, a polar organic solvent under ambient pressure or reduced pressure. Specifically, the dehydration step is performed by continuing the condensation reaction of the glycolic acid by continuing the heating of the mixture containing a reaction solution after the condensing step containing the glycolic acid, a depolymerization reaction solution and, if necessary, a polar organic solvent and/or a solubilizing agent under ambient pressure or reduced pressure. The used amount of the depolymerization reaction solution, the types, used amounts, or the like of the polar organic solvent and/or solubilizing agent are the same as those in the case when the polar organic solvent is used. With the method for preparing the GAO having a terminal carboxyl group concentration of 400 eq/t or less, the method comprising the dehydration step using the depolymerization reaction solution, since the polar organic solvent described above used in the dehydration step may be unnecessary or the used amount of the polar organic solvent can be reduced, the method is economically advantageous. Furthermore, since the depolymerization reaction solution used in the dehydration step typically contains the GAO and since the depolymerization reaction solution is typically at a high temperature condition that is a temperature exceeding 200° C., the preparation of the GAO having a terminal carboxyl group concentration of 400 eq/t or less can be performed economically as well as efficiently in terms of energy consumption.

2. Production of Glycolide by Heating Glycolic Acid Oligomer to Depolymerize

The present invention is a method for producing glycolide by heating a GAO to depolymerize, the method comprising the steps below:

I. a step 1 of heating a mixture containing a GAO having a terminal carboxyl group concentration of 400 eq/t or less and a polar organic solvent to a temperature for depolymerizing the GAO under ambient pressure or reduced pressure;

II. a step 2 of continuing the heating at the temperature for depolymerizing the GAO and then codistilling out, together with the polar organic solvent, glycolide produced by the depolymerization from the depolymerization reaction system containing the mixture; and III. a step 3 of obtaining glycolide from the codistillation product.

Step 1

The method for producing glycolide of the present invention by heating a GAO to depolymerize includes the step 1 of heating a mixture containing a GAO having a terminal carboxyl group concentration of 400 eq/t or less and a polar organic solvent to a GAO depolymerization temperature under ambient pressure or reduced pressure. The GAO having a terminal carboxyl group concentration of 400 eq/t or less is as described above, and as the polar organic solvent, solvents exemplified for the dehydration step described above can be used. The polar organic solvent is used in a proportion of typically 30 to 5000 parts by mass, and preferably 50 to 2000 parts by mass, per 100 parts by mass of the GAO. If the proportion of the polar organic solvent is too low, the depolymerization reactivity of the GAO decreases since the proportion of the solution phase of the GAO decreases (the proportion of the melt phase of the GAO increases) in the mixture containing the GAO and the polar organic solvent under the GAO depolymerization temperature condition. If the proportion of the polar organic solvent is too high, thermal efficiency in the depolymerization reaction decreases and productivity of the glycolide via the depolymerization reaction decreases. Note that, for cases where a polar organic solvent used in the dehydration step is remained in the GAO to be depolymerized, the used amount of the polar organic solvent refers to a total amount of a polar organic solvent and the remained polar organic solvent.

The mixture of the step 1 may further contain a solubilizing agent. As the solubilizing agent, solubilizing agents exemplified for the dehydration step described above can be used. When the solubilizing agent is contained, the solubilizing agent is used in a proportion of typically 0.1 to 500 parts by mass, and preferably 1 to 300 parts by mass, per 100 parts by mass of the GAO. Glycolide with higher purity can be obtained by adjusting the molar ratio of the GAO to the solubilizing agent (GAO/solubilizing agent) to a range of preferably 1 to 99, more preferably 3 to 70, and even more preferably 5 to 50. Furthermore, the mixture in the step 1 may further contain a catalyst. As the catalyst, a tin compound, such as tin chloride, an antimony compound, or the like can be used.

In the step 1, a mixture containing the GAO, the polar organic solvent, and, if necessary, the solubilizing agent and/or the catalyst is heated to a GAO depolymerization temperature under ambient pressure or reduced pressure. Although the GAO depolymerization temperature varies depending on the degree of pressure reduction or the type of the polar organic solvent, the GAO depolymerization temperature is typically at a temperature of 200° C. or higher. Therefore, the heating temperature is typically in a range of 200 to 350° C., preferably 210 to 310° C., more preferably 222 to 300° C., and particularly preferably 226 to 290° C.

In the step 1 of heating to a GAO depolymerization temperature, a solution phase of the GAO is preferably formed, and the depolymerization reaction is preferably performed in the conditions where the remaining proportion of the melt phase of the GAO is 0.5 or less, further preferably 0.3 or less, and particularly preferably 0. That is, the depolymerization reaction is particularly preferably performed in the condition where the remaining proportion of the melt phase of the GAO is substantially 0, that is the condition where the GAO is in a substantially uniform solution phase, from the perspective of efficiently obtaining highly pure glycolide.

Step 2

The method for producing glycolide of the present invention by heating a GAO to depolymerize includes the step 2 of continuing the heating at the heating temperature of the step 1 for depolymerizing the GAO and then codistilling out, together with the polar organic solvent, glycolide produced by the depolymerization from the depolymerization reaction system containing the mixture to the outside of the depolymerization reaction system. That is, in the step 2, by distilling the produced glycolide (boiling point in an atmospheric pressure=240 to 241° C.) together with the polar organic solvent, plugging of the line due to glycolide deposited and attached to the inner wall of the distillation line is avoided, thereby making it possible to continue the depolymerization reaction for a long period of time. Since the depolymerization reaction of the GAO is a reversible reaction, the depolymerization reaction of the GAO progresses efficiently when glycolide is distilled out from the depolymerization reaction system to the outside of the depolymerization reaction system.

The heating in the step 2 is performed under ambient pressure or reduced pressure; however, from the perspective of enabling the depolymerization reaction to take place at a low temperature, the heating is preferably performed under reduced pressure of 0.1 to 90 kPa (0.75 to 675 mmHg), more preferably 1 to 60 kPa (7.5 to 450 mmHg), even more preferably 1.5 to 40 kPa (11.3 to 300 mmHg), and particularly preferably 2 to 30 kPa (15 to 225 mmHg). Furthermore, by adjusting the amount of heat input, the amount of glycolide that is codistilled out with the polar organic solvent to the outside of the depolymerization reaction system can be adjusted.

Step 3

The method for producing glycolide of the present invention by heating a GAO to depolymerize includes the step 3 of obtaining glycolide from the codistillation product after the step 2 of codistilling the glycolide together with the polar organic solvent to the outside of the depolymerization reaction system. Specifically, the codistillation product is cooled using a heat exchanger (condenser) to be liquefied and phase separation of the glycolide and the polar organic solvent is performed in the liquid state. When the codistillation product is subjected to the phase separation, a glycolide phase (glycolide layer) is formed in the lower layer and a polar organic solvent phase (layer containing the polar organic solvent) is formed in the upper layer. The glycolide can be obtained by separating and recovering the glycolide in the lower layer as a liquid. Note that, as described above, the amount of the obtained glycolide can be adjusted by adjusting the amount of heat input. In order to perform phase separation on the glycolide and the polar organic solvent in the liquid state, the cooling temperature is typically controlled to a range of 70 to 180° C., preferably 75 to 150° C., and more preferably 80 to 120° C. When the cooling temperature is too high, side reactions such as a ring-opening reaction tend to occur in the glycolide phase during the separation and recovery operation. When the cooling temperature is too low, it becomes difficult to perform phase separation in the liquid state.

When the depolymerization reaction is continued while controlling the temperature of the codistillation product with the heat exchanger, the glycolide that is codistilled out together with the polar organic solvent passes through the solvent phase of the codistillation product upper layer in the form of liquid droplets and is condensed in the glycolide phase of the lower layer. The rest of the polar organic solvent phase after removing the glycolide from the codistillation product can be reused by discharging it to the outside of the depolymerization reaction system. The polar organic solvent may be reused after being purified by adsorption using activated carbon or after being purified by distillation. When polyalkylene glycol diether having excellent thermal stability is used as the polar organic solvent, substantially the total amount of the polar organic solvent recovered from the codistillation product can be reused without purification.

Depolymerization Reaction Solution

In the step 2, after the glycolide that is produced by the depolymerization is codistilled out together with the polar organic solvent to the outside of the depolymerization reaction system, the depolymerization reaction solution, which remains in the depolymerization reaction system, contains the GAO, various by-products (impurities), and the like in addition to the polar organic solvent or the solubilizing agent that is contained as necessary. As described above, by using the depolymerization reaction solution obtained from this depolymerization reaction system in the dehydration step, the GAO having a terminal carboxyl group concentration of 400 eq/t or less can be prepared. As the depolymerization reaction solution used in the dehydration step, the depolymerization reaction solution obtained from the depolymerization reaction system in which the method for producing glycolide including the step 2 has been performed once or for multiple times can be used; however, the depolymerization reaction solution obtained from another depolymerization reaction system can be also used.

According to the method for producing glycolide of the present invention, highly pure glycolide can be obtained without performing total reflux treatment that involves new thermal history. The obtained glycolide may be purified by further performing recrystallization or washing if particularly desired; however, since highly pure glycolide is obtained, there is no need to use a large amount of solvent for the purification, and the separation operation of glycolide from the solvent is simplified. Meanwhile, substantially all the amount of the mother liquor after removal of glycolide (fraction containing the polar organic solvent) can be reused without going through another step such as purification. The mother liquor may be reused after purifying the fraction containing the polar organic solvent by adsorption using activated carbon or by distillation.

The glycolide obtained by the method for producing glycolide of the present invention (hereinafter, also referred to as "crude glycolide") has purity of 85% or higher from the initial stage of the depolymerization reaction. For example, for cases such that a glycolic acid oligomer having a terminal carboxyl group concentration of 400 eq/t or lower is used as the raw material, the obtained glycolide is highly pure glycolide preferably having purity of 90% or higher, and more preferably 91% or higher. Furthermore, since the production speed of glycolide does not decrease and plugging of the distillation line does not occur, continuous operation of the glycolide production for a long time period is possible.

EXAMPLES

The present invention will be described in further detail hereinafter using reference examples, working examples, a comparative example, and a control; however, the present invention is not limited to these examples. The measurement methods for the physical properties of the GAO or glycolide are as follows.

Melting Point of Glycolic Acid Oligomer

The melting point of the GAO was measured by heating at a rate of temperature increase of 10° C./min in an inert gas atmosphere using a differential scanning calorimeter (DSC). The same applied for a mixture containing the GAO.

Terminal Carboxyl Group Concentration of Glycolic Acid Oligomer

The terminal carboxyl group concentration of the GAO was measured and calculated by the following method. That is, 0.1 g of GAO sample was completely dissolved in 10 mL of special grade dimethylsulfoxide in an oil bath at 150° C. for approximately 3 minutes to form a solution. After adding two drops of an indicator (0.1% by mass of bromothymol blue/alcohol solution) to this solution, 0.05 N of diazabicycloundecene/dimethylsulfoxide solution was added until an end point, where color of the solution had changed from yellow to blue when observed visually, was reached. From the dropped amount of the indicator at the point, the terminal carboxyl group concentration was calculated as the equivalent amount (eq) per 1 ton (t) of the GAO. Furthermore, the terminal carboxyl group concentration of the GAO contained in the mixture containing the GAO and the polar organic solvent was measured by the following method. That is, 0.1 g of the mixture was completely dissolved in 10 mL of special grade dimethylsulfoxide in an oil bath at a temperature of 150° C. for approximately 3 minutes to form a solution. After adding two drops of the indicator described above to this solution, 0.009 N of diazabicycloundecene/dimethylsulfoxide solution was added until an end point, where color of the solution had changed from yellow to blue when observed visually, was reached. From the dropped amount of the indicator at the point, the terminal carboxyl group concentration of the GAO was calculated as the equivalent amount (eq) per 1 ton (t) of the mixture, and then, by dividing the calculated equivalent amount by the mass proportion of the GAO in the mixture, the terminal carboxyl group concentration of the GAO was calculated as the equivalent amount (eq) per 1 ton (t) of the GAO.

Purity of Glycolide

The purity of glycolide produced by a depolymerization reaction was measured by gas chromatography (GC). Specifically, 200 mg of glycolide sample and 40 mg of p-chlorobenzophenone (manufactured by Tokyo Chemical Industry Co., Ltd.) serving as an internal standard substance were, first, dissolved in 10 mL of acetone. Next, 2 μL of the solution was collected and injected into a gas chromatography device, and the amount of glycolide was measured under the following conditions. A calibration curve created in advance using glycolide and p-chlorobenzophenone serving as the internal standard substance was used to determine the purity of the glycolide.

<GC Conditions>
Measurement device: "GC-2010" manufactured by Shimadzu Corporation
Column: capillary column TC-17, 0.25 mm ϕ×30 mm
Column temperature: 280° C.
Injection temperature: 150° C.

Reference Example 1

Method for Producing GAO (Present Invention)

In a flask with a volume of 500 mL, 400 g of glycolic acid 70% aqueous solution (manufactured by DuPont) was charged and heated from the room temperature to a temperature of 210° C. for 4 hours while being stirred in the ambient pressure. Thereby, condensation reaction was performed to produce GAO while water is distilled (condensing step). Then, after 60 g of tetraethylene glycol dibutyl ether as a polar organic solvent and 60 g of octyl triethylene glycol as a solubilizing agent were added, the pressure was reduced slowly for 1 hour from the ambient pressure to 3 kPa (22.5 mmHg) while the temperature of 210° C. was maintained. Low-boiling point components such as water and unreacted raw materials were distilled off by further continuing the condensation reaction for 8 hours, 312 g of a mixture containing the polar organic solvent and 192 g of the GAO was prepared (dehydration step). The GAO contained in the obtained mixture had a terminal carboxyl group concentration of 240 eq/t and a melting point (measured for the mixture; hereinafter the same) of 206° C.

Reference Example 2

Method for Producing GAO (Present Invention)

In a flask with a volume of 500 mL, 400 g of glycolic acid 70% aqueous solution (manufactured by DuPont) was charged and heated from the room temperature to a temperature of 215° C. for 4 hours while being stirred in the ambient pressure. Thereby, condensation reaction was performed to produce GAO while water is distilled (condensing step). Then, after 60 g of tetraethylene glycol dibutyl ether and 60 g of octyl triethylene glycol were added, the pressure was reduced slowly for 1 hour from the ambient pressure to 3 kPa while the temperature of 215° C. was maintained. Low-boiling point components such as water and unreacted raw materials were distilled off by further continuing the condensation reaction for 6 hours, 312 g of a mixture containing the polar organic solvent and 192 g of the GAO was prepared (dehydration step). The GAO contained in the obtained mixture had a terminal carboxyl group concentration of 213 eq/t and a melting point of 212° C.

Reference Example 3

Method for Producing GAO (Present Invention)

In a flask with a volume of 500 mL, 400 g of glycolic acid 70% aqueous solution (manufactured by DuPont) was charged and heated from the room temperature to a temperature of 220° C. for 4 hours while being stirred in the ambient pressure. Thereby, condensation reaction was performed to produce GAO while water is distilled (condensing step). Then, after 60 g of tetraethylene glycol dibutyl ether and 60 g of octyl triethylene glycol were added, the pressure was reduced slowly for 1 hour from the ambient pressure to 3 kPa while the temperature of 220° C. was maintained. Low-boiling point components such as water and unreacted raw materials were distilled off by further continuing the condensation reaction for 6 hours, 312 g of a mixture containing the polar organic solvent and 192 g of the GAO was prepared (dehydration step). The GAO contained in the obtained mixture had a terminal carboxyl group concentration of 187 eq/t and a boiling point of 210° C.

Reference Example 4

Method for Producing GAO (Present Invention)

In a flask with a volume of 500 mL, 400 g of glycolic acid 70% aqueous solution (manufactured by DuPont) was charged and heated from the room temperature to a temperature of 220° C. for 4 hours while being stirred in the ambient pressure. Thereby, condensation reaction was performed to produce GAO while water is distilled (condensing step). Then, after 60 g of tetraethylene glycol dibutyl ether, 60 g of octyl triethylene glycol, and 64.5 mg of tin chloride as a catalyst were added, the pressure was reduced slowly for 1 hour from the ambient pressure to 3 kPa while the temperature of 220° C. was maintained. Low-boiling point components such as water and unreacted raw materials were distilled off by further continuing the condensation reaction for 6 hours, 312 g of a mixture containing the polar organic solvent and 192 g of the GAO was prepared (dehydration step). The GAO contained in the obtained mixture had a terminal carboxyl group concentration of 114 eq/t and a melting point of 213° C.

Reference Example 5

Method for Producing GAO (Comparative Example)

In a flask with a volume of 500 mL, 400 g of glycolic acid 70% aqueous solution (manufactured by DuPont) was charged and heated from the room temperature to a temperature of 220° C. for 4 hours while being stirred in the ambient pressure. Thereby, condensation reaction was performed to produce GAO while water is distilled. Then, the pressure was reduced slowly for 1 hour from the ambient pressure to 3 kPa while the temperature of 220° C. was maintained. Low-boiling point components such as water and unreacted raw materials were distilled off by further continuing the condensation reaction for 3 hours, 192 g of the GAO was prepared. The obtained GAO had a terminal carboxyl group concentration of 527 eq/t and a melting point of 217° C.

Working Example 1

In a flask with a volume of 500 mL, 150 g of the mixture containing the GAO and the polar organic solvent prepared in Reference Example 1, 40 g of tetraethylene glycol dibutyl ether as a polar organic solvent, and 40 g of octyl triethylene glycol as a solubilizing agent were charged and heated to a temperature of 235° C. in the ambient pressure to make the reaction system a uniform solution (step 1). For this solution, by reducing the pressure to 4.5 kPa (33.8 mmHg) while the temperature was maintained at 235° C., the tetraethylene glycol dibutyl ether and the produced glycolide were codistilled. When the depolymerization reaction was performed continuously for 1 hour while the amount of heat input was adjusted (step 2), no plugging of the line was observed. From the codistillation product, 12.8 g of glycolide was obtained (step 3). The purity of the glycolide was 91.5%.

Working Example 2

The tetraethylene glycol dibutyl ether and the produced glycolide were codistilled in the same manner as in Working Example 1 except for using 150 g of the mixture containing the GAO and the polar organic solvent prepared in Reference Example 2 in place of the GAO prepared in Reference Example 1. From the codistillation product, 12.8 g of glycolide was obtained. No plugging of the line was observed, and the purity of the glycolide was 92.4%.

Working Example 3

The tetraethylene glycol dibutyl ether and the produced glycolide were codistilled in the same manner as in Working Example 1 except for using 150 g of the mixture containing the GAO and the polar organic solvent prepared in Reference Example 3 in place of the GAO prepared in Reference Example 1. From the codistillation product, 13.1 g of glycolide was obtained. No plugging of the line was observed, and the purity of the glycolide was 93.3%.

Working Example 4

The tetraethylene glycol dibutyl ether and the produced glycolide were codistilled in the same manner as in Working Example 1 except for using 150 g of the mixture containing the GAO and the polar organic solvent prepared in Reference Example 4 in place of the GAO prepared in Reference Example 1. From the codistillation product, 17.4 g of glycolide was obtained. No plugging of the line was observed, and the purity of the glycolide was 96.2%.

Comparative Example 1

In a flask with a volume of 500 mL, 160 g of the GAO prepared in Reference Example 5, 100 g of tetraethylene glycol dibutyl ether, and 89 g of octyl triethylene glycol were charged and heated to a temperature of 230° C. in the ambient pressure to make the reaction system a uniform solution (step 1). For this solution, by reducing the pressure to 4.5 kPa (33.8 mmHg) while the temperature was maintained at 230° C., the tetraethylene glycol dibutyl ether and the produced glycolide were codistilled. When the reaction was performed continuously for 1 hour (step 2), some plugging of the line was observed. From the codistillation product, 12.5 g of glycolide was obtained (step 3). The purity of the glycolide was 81.2%.

[Control 1] (Total Reflux Treatment)

In a flask with a volume of 500 mL, 160 g of the GAO prepared in Reference Example 5, 100 g of tetraethylene glycol dibutyl ether, and 89 g of octyl triethylene glycol were charged and heated to a temperature of 225° C. in the ambient pressure to make the reaction system a uniform solution. For this solution, the pressure was slowly reduced to 3 kPa for 1 hour while the temperature was maintained at 225° C., and total reflux treatment was performed for 5 hours. Thereby, 347 g of a mixture containing the polar organic solvent and 158 g of the GAO was prepared. The GAO contained in this mixture had a terminal carboxyl group concentration of 170 eq/t and a melting point of 211° C.

The tetraethylene glycol dibutyl ether and the produced glycolide were codistilled in the same manner as in Working Example 1 except for using 150 g of the mixture containing the GAO and the polar organic solvent prepared by subjecting the GAO prepared in Reference Example 5 to the total reflux treatment in place of the mixture containing the GAO and the polar organic solvent prepared in Reference Example 1. From the codistillation product, 13.0 g of glycolide was obtained. No plugging of the line was observed, and the purity of the glycolide was 93.9%.

For Working Examples 1 to 4, Comparative Example 1, and Control 1, the terminal carboxyl group concentration (hereinafter, also referred to as "terminal COOH") and melting point of the GAO used in the depolymerization, the production method of the GAO, presence or absence of total reflux treatment, depolymerization conditions, and the yield and purity of the obtained glycolide (hereinafter, also referred to as "GL") are shown in Table 1.

TABLE 1

| | | | Working Example 1 | Working Example 2 | Working Example 3 |
|---|---|---|---|---|---|
| GAO | | Terminal COOH (eq/t) | 240 | 213 | 187 |
| | | Melting point (° C.) | 206 | 212 | 210 |
| Production of GAO | | Production method | Reference Example 1 | Reference Example 2 | Reference Example 3 |
| | Condensing step | Temperature (° C.) | 210 | 215 | 220 |
| | | Pressure (kPa) | Ambient pressure | Ambient pressure | Ambient pressure |
| | | Heating time (hour) | 4 | 4 | 4 |
| | Dehydration step | Polar organic solvent | Present | Present | Present |
| | | Temperature (° C.) | 210 | 215 | 220 |
| | | Pressure (kPa) | 3 | 3 | 3 |
| | | Reaction time (hour) | 8 | 6 | 6 |
| | | Presence or absence of catalyst | — | — | — |
| Total reflux treatment | | Temperature (° C.) | (No total reflux) | (No total reflux) | (No total reflux) |
| | | Pressure (kPa) | | | |
| | | Treatment time (hour) | | | |
| | GAO | Terminal COOH (eq/t) | | | |
| | | Melting point (° C.) | | | |
| Depolymerization | | Temperature (° C.) | 235 | 235 | 235 |
| | | Pressure (kPa) | 4.5 | 4.5 | 4.5 |
| | | Depolymerization time (hour) | 1 | 1 | 1 |
| | | Yield of GL (g) | 12.8 | 12.8 | 13.1 |
| | | Purity of GL (%) | 91.5 | 92.4 | 93.3 |

| | | | Working Example 4 | Comparative Example 1 | Control 1 |
|---|---|---|---|---|---|
| GAO | | Terminal COOH (eq/t) | 114 | 527 | 527 |
| | | Melting point (° C.) | 213 | 217 | 217 |
| Production of GAO | | Production method | Reference Example 4 | Reference Example 5 | Reference Example 5 |
| | Condensing step | Temperature (° C.) | 220 | 220 | 220 |
| | | Pressure (kPa) | Ambient pressure | Ambient pressure | Ambient pressure |
| | | Heating time (hour) | 4 | 4 | 4 |
| | Dehydration step | Polar organic solvent | Present | — | — |
| | | Temperature (° C.) | 220 | 220 | 220 |
| | | Pressure (kPa) | 3 | 3 | 3 |
| | | Reaction time (hour) | 6 | 3 | 3 |
| | | Presence or absence of catalyst | Present | — | — |
| Total reflux treatment | | Temperature (° C.) | (No total reflux) | (No total reflux) | 225 |
| | | Pressure (kPa) | | | 3 |
| | | Treatment, time (hour) | | | 5 |
| | GAO | Terminal COOH (eq/t) | | | 170 |
| | | Melting point (° C.) | | | 211 |
| Depolymerization | | Temperature (° C.) | 235 | 230 | 235 |
| | | Pressure (kPa) | 4.5 | 4.5 | 4.5 |
| | | Depolymerization time (hour) | 1 | 1 | 1 |
| | | Yield of GL (g) | 17.4 | 12.5 | 13.0 |
| | | Purity of GL (%) | 96.2 | 81.2 | 93.9 |

From Table 1, it was confirmed that the method for producing glycolide by heating a GAO to depolymerize, the method comprising the steps below, of Working Examples 1 to 4:

I. a step 1 of heating a mixture containing a GAO having a terminal carboxyl group concentration of 400 eq/t or less and a polar organic solvent to a temperature for depolymerizing the GAO under ambient pressure or reduced pressure;
II. a step 2 of continuing the heating at the temperature for depolymerizing the GAO and then codistilling out, together with the polar organic solvent, glycolide produced by the depolymerization from the depolymerization reaction system containing the mixture; and
III. a step 3 of obtaining glycolide from the codistillation product;

can provide highly pure glycolide of purity of 85% or higher, and preferably 90% or higher, via depolymerization, while the method involves no new thermal history due to total reflux treatment, contributes to energy conservation, lowers the amount of impurities in the distillate that is distilled from the depolymerization reaction system, and suppresses the plugging of the line due to oligomerization of glycolide caused by impurities.

It was confirmed that, by the methods for producing a GAO of Reference Examples 1 to 4 comprising a condensing step of subjecting glycolic acid to condensation reaction by heating the glycolic acid under ambient pressure or reduced pressure, and a dehydration step of continuing the condensation reaction of the glycolic acid by continuing the heating together with a polar organic solvent under ambient pressure or reduced pressure, a GAO having a terminal carboxyl group concentration of 400 eq/t or less, and preferably 250 eq/t or less, can be efficiently prepared. Furthermore, it was also confirmed that GAOs prepared by the methods for producing a GAO of Reference Examples 1 to 4 can provide, at high yield, highly pure glycolide having a purity that is equivalent to or better than that of glycolide obtained by heating a total reflux-treated GAO to depolymerize even without performing total reflux treatment, which involves thermal history again, on the once prepared GAO.

Furthermore, from Working Example 4, it was confirmed that extremely highly pure glycolide can be obtained at even higher yield when the GAO is prepared by performing the dehydration step in the presence of a catalyst and then depolymerized.

On the other hand, with the method for producing glycolide of Comparative Example 1, in which a GAO having a terminal carboxyl group concentration of 527 eq/t is heated to depolymerize, since the purity of the obtained glycolide is low, it was confirmed that it is necessary to perform a purification operation to enhance the purity of the glycolide, and that the depolymerization of the GAO may not be continued for a long period of time since plugging of the line due to oligomerization of the glycolide easily occurs because of the large amount of impurities other than glycolide. Note that, as in Control 1, in the method for producing glycolide that depolymerize a GAO that has undergone total reflux treatment, by which thermal history is added again (at a temperature of 225° C. for 5 hours) once it was prepared, it was confirmed that the temperature at which the total reflux treatment is performed needs to be set high.

Reference Example 6

Method for Producing GAO (Present Invention)

In a flask with a volume of 500 mL, 300 g of glycolic acid 70% aqueous solution (manufactured by DuPont) was charged and heated from the room temperature to a temperature of 220° C. for 4 hours while being stirred in the ambient pressure. Thereby, condensation reaction was performed to produce GAO while water is distilled (condensing step). Then, after the pressure was reduced from the ambient pressure to 10 kPa while the temperature of 220° C. was maintained, 165 g of depolymerization reaction solution obtained from the depolymerization reaction system after repeating the step 2 of the method for producing glycolide of Working Example 1, was added. Thereafter, the pressure was slowly reduced for 1 hour to 3 kPa. Low-boiling point components such as water and unreacted raw materials were distilled off by further continuing the condensation reaction for 3 hours, 309 g of a mixture containing the polar organic solvent and 210 g of the GAO was prepared (dehydration step). The GAO contained in the obtained mixture had a terminal carboxyl group concentration of 390 eq/t.

Reference Example 7

Method for Producing GAO (Present Invention)

In the same manner as in Reference Example 6, 309 g of the mixture containing the polar organic solvent and 210 g of the GAO was prepared except for continuing the condensation reaction for 5 hours in the dehydration step. The GAO contained in the obtained mixture had a terminal carboxyl group concentration of 352 eq/t.

Reference Example 8

Method for Producing GAO (Present Invention)

In the same manner as in Reference Example 6, 357 g of the mixture containing the polar organic solvent and 210 g of the GAO was prepared except for adding 165 g of the depolymerization reaction solution, 24 g of tetraethylene glycol dibutyl ether, and 24 g of octyl triethylene glycol, and continuing the condensation reaction for 6 hours in the dehydration step. The GAO contained in the obtained mixture had a terminal carboxyl group concentration of 233 eq/t.

Reference Example 9

Method for Producing GAO (Present Invention)

In the same manner as in Reference Example 6, 357 g of the mixture containing the polar organic solvent and 210 g of the GAO was prepared except for adding 165 g of the depolymerization reaction solution, 24 g of tetraethylene glycol dibutyl ether, 24 g of octyl triethylene glycol, and 59.4 mg of tin chloride as a catalyst, and continuing the condensation reaction for 6 hours in the dehydration step. The GAO contained in the obtained mixture had a terminal carboxyl group concentration of 150 eq/t.

Working Example 5

In a flask with a volume of 500 mL, 150 g of the mixture containing the GAO and the polar organic solvent prepared in Reference Example 6, 60 g of tetraethylene glycol dibutyl ether as a polar organic solvent, and 60 g of octyl triethylene glycol as a solubilizing agent were charged and heated to a temperature of 235° C. in the ambient pressure to make the reaction system a uniform solution (step 1). For this solution, by reducing the pressure to 4.5 kPa (33.8 mmHg) while the temperature was maintained at 235° C., the tetraethylene glycol dibutyl ether and the produced glycolide were codistilled. When the depolymerization reaction was performed continuously for 1 hour while the amount of heat input was adjusted (step 2), no plugging of the line was observed. From the codistillation product, 12.6 g of glycolide was obtained (step 3). The purity of the glycolide was 86.6%.

Working Example 6

The tetraethylene glycol dibutyl ether and the produced glycolide were codistilled in the same manner as in Working Example 5 except for using 150 g of the mixture containing the GAO and the polar organic solvent prepared in Reference Example 7 in place of the GAO prepared in Reference Example 6. From the codistillation product, 12.7 g of glycolide was obtained. No plugging of the line was observed, and the purity of the glycolide was 90.1%.

Working Example 7

The tetraethylene glycol dibutyl ether and the produced glycolide were codistilled in the same manner as in Working Example 5 except for using 150 g of the mixture containing the GAO and the polar organic solvent prepared in Reference Example 8 in place of the GAO prepared in Reference Example 6, and charging 55 g of tetraethylene glycol dibutyl ether as a polar organic solvent, and 55 g of octyl triethylene glycol as a solubilizing agent. From the codistillation product, 11.3 g of glycolide was obtained. No plugging of the line was observed, and the purity of the glycolide was 90.5%.

Working Example 8

The tetraethylene glycol dibutyl ether and the produced glycolide were codistilled in the same manner as in Working Example 7 except for using 150 g of the mixture containing the GAO and the polar organic solvent prepared in Reference Example 9 in place of the GAO prepared in Reference Example 8. From the codistillation product, 12.0 g of glycolide was obtained. No plugging of the line was observed, and the purity of the glycolide was 93.0%.

For Working Examples 5 to 8, the terminal COOH of the GAO used in the depolymerization, the production method of the GAO, presence or absence of total reflux treatment, depolymerization conditions, and the yield and purity of the obtained glycolide (GL) are shown in Table 2.

TABLE 2

| | | | Working Example 5 | Working Example 6 |
|---|---|---|---|---|
| GAO | | Terminal COOH (eq/t) | 390 | 352 |
| Production of GAO | | Production method | Reference Example 6 | Reference Example 7 |
| | Condensing step | Temperature (° C.) | 220 | 220 |
| | | Pressure (kPa) | Ambient pressure | Ambient pressure |
| | | Heating time (hour) | 4 | 4 |
| | Dehydration step | Depolymerization reaction solution | Present | Present |
| | | Polar organic solvent | — | — |
| | | Temperature (° C.) | 220 | 220 |
| | | Pressure (kPa) | 3 | 3 |
| | | Reaction time (hour) | 3 | 5 |
| | | Presence or absence of catalyst | — | — |
| Total reflux treatment | | Temperature (° C.) | (No total reflux) | (No total reflux) |
| | | Pressure (kPa) | | |
| | | Treatment time (hour) | | |
| | | Terminal COOH of GAO (eq/t) | | |
| Depolymerization | | Temperature (° C.) | 235 | 235 |
| | | Pressure (kPa) | 4.5 | 4.5 |
| | | Depolymerization time (hour) | 1 | 1 |
| | | Yield of GL (g) | 12.6 | 12.7 |
| | | Purity of GL (%) | 86.6 | 90.1 |

| | | | Working Example 7 | Working Example 8 |
|---|---|---|---|---|
| GAO | | Terminal COOH (eq/t) | 233 | 150 |
| Production of GAO | | Production method | Reference Example 8 | Reference Example 9 |
| | Condensing step | Temperature (° C.) | 220 | 220 |
| | | Pressure (kPa) | Ambient pressure | Ambient pressure |
| | | Heating time (hour) | 4 | 4 |
| | Dehydration step | Depolymerization reaction solution | Present | Present |
| | | Polar organic solvent | Present | Present |
| | | Temperature (° C.) | 220 | 220 |
| | | Pressure (kPa) | 3 | 3 |
| | | Reaction time (hour) | 6 | 6 |
| | | Presence or absence of catalyst | — | Present |
| Total reflux treatment | | Temperature (° C.) | (No total reflux) | (No total reflux) |
| | | Pressure (kPa) | | |
| | | Treatment time (hour) | | |
| | | Terminal COOH of GAO (eq/t) | | |
| Depolymerization | | Temperature (° C.) | 235 | 235 |
| | | Pressure (kPa) | 4.5 | 4.5 |
| | | Depolymerization time (hour) | 1 | 1 |
| | | Yield of GL (g) | 11.3 | 12.0 |
| | | Purity of GL (%) | 90.5 | 93.0 |

From Table 2, it was confirmed that the method for producing glycolide by heating a GAO to depolymerize, the method comprising the steps below, of Working Examples 5 to 8:

I. a step 1 of heating a mixture containing a GAO having a terminal carboxyl group concentration of 400 eq/t or less and a polar organic solvent to a temperature for depolymerizing the GAO under ambient pressure or reduced pressure;
II. a step 2 of continuing the heating at the temperature for depolymerizing the GAO and then codistilling out, together with the polar organic solvent, glycolide produced by the depolymerization from the depolymerization reaction system containing the mixture; and
III. a step 3 of obtaining glycolide from the codistillation product;
can provide highly pure glycolide of purity of 85% or higher via depolymerization, while the method involves no thermal history due to total reflux treatment, contributes to energy conservation, lowers the amount of impurities in the distillate that is distilled from the depolymerization reaction system, and suppresses the plugging of the line due to oligomerization of glycolide caused by impurities.

Furthermore, it was confirmed that the GAO having the terminal carboxyl group concentration of 400 eq/t or less can be efficiently prepared by methods for producing a GAO of Reference Examples 6 to 9 comprising a condensing step of subjecting glycolic acid to condensation reaction by heating the glycolic acid under ambient pressure or reduced pressure, and a dehydration step of continuing the condensation reaction of the glycolic acid by continuing the heating together with a depolymerization reaction solution obtained from a depolymerization reaction system and, if necessary, the polar organic solvent under ambient pressure or reduced pressure. Furthermore, it was also confirmed that GAOs prepared by the methods for producing a GAO of Reference Examples 6 to 9 can provide highly pure glycolide at high yield even without performing total reflux treatment, which involves thermal history again, on the once prepared GAO.

Furthermore, from Working Example 8, it was confirmed that even more highly pure glycolide can be obtained at high yield when GAO is prepared by performing the dehydration step in the presence of a catalyst and then depolymerized.

INDUSTRIAL APPLICABILITY

Since the present invention is a method for producing glycolide by heating a glycolic acid oligomer to depolymerize, the method comprising the steps below:
I. a step 1 of heating a mixture containing a glycolic acid oligomer having a terminal carboxyl group concentration of 400 eq/t or less and a polar organic solvent to a temperature for depolymerizing the glycolic acid oligomer under ambient pressure or reduced pressure;
II. a step 2 of continuing the heating at the temperature for depolymerizing the glycolic acid oligomer and then codistilling out, together with the polar organic solvent, glycolide produced by the depolymerization from the depolymerization reaction system containing the mixture; and
III. a step 3 of obtaining glycolide from the codistillation product;
the present invention can provide a method for producing glycolide that provides highly pure glycolide via depolymerization, the method involving no new thermal history due to total reflux treatment, contributing to energy conservation, lowering the amount of impurities in the distillate that is distilled from the depolymerization reaction system, and suppressing the plugging of the line due to oligomerization of glycolide caused by impurities.

In particular, since the present invention can provide a method for producing glycolide that can efficiently prepare a glycolic acid oligomer having a terminal carboxyl group concentration of 400 eq/t or less by a method for producing a glycolic acid oligomer comprising a condensing step of subjecting glycolic acid to condensation reaction by heating the glycolic acid under ambient pressure or reduced pressure, and a dehydration step of continuing the condensation reaction of the glycolic acid by continuing the heating together with a polar organic solvent or a depolymerization reaction solution under ambient pressure or reduced pressure, and since the present invention can provide highly pure glycolide at high yield even without performing total reflux treatment, which involves thermal history again, on the prepared GAO, the present invention has excellent industrial applicability.

The invention claimed is:

1. A method for producing glycolide by heating a glycolic acid oligomer to depolymerize, the method comprising steps below:
   I. a step 1 of heating a mixture containing a glycolic acid oligomer having a terminal carboxyl group concentration of 400 eq/t or less and a polar organic solvent to a temperature for depolymerizing the glycolic acid oligomer under ambient pressure or reduced pressure;
   II. a step 2 of continuing the heating at the temperature for depolymerizing the glycolic acid oligomer and then codistilling out, together with the polar organic solvent, glycolide produced by the depolymerization from a depolymerization reaction system containing the mixture; and
   III. a step 3 of obtaining glycolide from the codistillation product,
   wherein the glycolic acid oligomer having the terminal carboxyl group concentration of 400 eq/t or less is prepared by a method for producing a glycolic acid oligomer comprising a condensing step of subjecting glycolic acid to condensation reaction by heating the glycolic acid under ambient pressure or reduced pressure, and a dehydration step of continuing the condensation reaction of the glycolic acid by continuing the heating together with a polar organic solvent under ambient pressure or reduced pressure.

2. The method for producing glycolide according to claim 1, wherein the glycolic acid oligomer having the terminal carboxyl group concentration of 400 eq/t or less is prepared by a method for producing a glycolic acid oligomer comprising a condensing step of subjecting glycolic acid to condensation reaction by heating the glycolic acid under ambient pressure or reduced pressure, and a dehydration step of continuing the condensation reaction of the glycolic acid by continuing the heating together with a depolymerization reaction solution obtained from a depolymerization reaction system under ambient pressure or reduced pressure.

3. The method for producing glycolide according to claim 1, wherein the dehydration step is performed in the presence of a solubilizing agent.

4. The method for producing glycolide according to claim 1, wherein the mixture in the step 1 contains a solubilizing agent.

5. The method for producing glycolide according to claim 1, wherein the dehydration step is performed in the presence of a catalyst.

6. The method for producing glycolide according to claim 1, wherein the polar organic solvent is polyalkylene glycol diether having a molecular weight of 150 to 450.

7. The method for producing glycolide according to claim 3, wherein the solubilizing agent is polyalkylene glycol monoether having a boiling point of 180° C. or higher.

* * * * *